United States Patent
Uzbelger Feldman

(12) 
(10) Patent No.: US 10,898,070 B2
(45) Date of Patent: Jan. 26, 2021

(54) IMAGING APPARATUS AND METHODS

(71) Applicant: REAL TIME IMAGING TECHNOLOGIES, LLC, Charlotte, NC (US)

(72) Inventor: Daniel Uzbelger Feldman, Beachwood, OH (US)

(73) Assignee: REAL TIME IMAGING TECHNOLOGIES, LLC, Charlotte, NC (US)

( * ) Notice: Subject to any disclaimer, the term of this patent is extended or adjusted under 35 U.S.C. 154(b) by 864 days.

(21) Appl. No.: 14/989,748

(22) Filed: Jan. 6, 2016

(65) Prior Publication Data

US 2016/0113483 A1  Apr. 28, 2016

Related U.S. Application Data

(63) Continuation of application No. PCT/US2013/049504, filed on Jul. 7, 2013.

(51) Int. Cl.
| | | |
|---|---|---|
| A61B 6/14 | (2006.01) | |
| A61B 1/24 | (2006.01) | |
| A61B 5/00 | (2006.01) | |
| A61B 1/05 | (2006.01) | |
| A61B 1/00 | (2006.01) | |
| A61B 90/00 | (2016.01) | |

(52) U.S. Cl.
CPC .......... *A61B 1/24* (2013.01); *A61B 1/00186* (2013.01); *A61B 1/051* (2013.01); *A61B 5/0073* (2013.01); *A61B 5/0088* (2013.01); *A61B 6/14* (2013.01); *A61B 2090/376* (2016.02); *A61B 2576/00* (2013.01)

(58) Field of Classification Search
CPC ...... A61B 6/145; A61B 6/4208; G01T 1/2002
See application file for complete search history.

(56) References Cited

U.S. PATENT DOCUMENTS 6,002,743 A * 12/1999 Telymonde ........... G06T 1/0007
378/98.8
7,138,633 B1 * 11/2006 Rozsa .................. G01T 1/1648
250/368

(Continued)

FOREIGN PATENT DOCUMENTS

JP  2002350547 A  * 12/2002

OTHER PUBLICATIONS

English translation of TW Application No. 101143908 filed on Nov. 23, 2012 (Year: 2012).*

*Primary Examiner* — Chih-Cheng Kao
(74) *Attorney, Agent, or Firm* — Chad D Tillman; Jeremy C Doerre; Tillman Wright

(57) ABSTRACT

A microlens in radiography in providing healthcare services, including medical and dental fields. The microlens preferably is included as a component of a detector. The detector preferably comprises a converter, a plate, a filter, the microlens, and a collector including photosensitive areas. Low light images are received at the converter and transmitted directly or through the plate to the filter and then to the microlens. The microlens collects, refines and focuses the low light image that would have otherwise fallen onto the non-sensitive areas of the collector, thereby enabling low light detection efficiency at the sensitive areas, and thereby increasing the collector fill factor and quantum efficiency.

20 Claims, 5 Drawing Sheets

(56) References Cited

U.S. PATENT DOCUMENTS

| | | | | |
|---|---|---|---|---|
| 8,437,085 B1* | 5/2013 | Zhovnirovsky | ...... | G02B 3/0056 359/619 |
| 2009/0179142 A1* | 7/2009 | Duparre | ............... | G02B 3/0031 250/208.1 |
| 2009/0238330 A1* | 9/2009 | Luhta | .................... | A61B 6/032 378/19 |
| 2011/0150185 A1* | 6/2011 | Uzbelger Feldman | .. | A61B 6/14 378/191 |
| 2012/0148031 A1* | 6/2012 | Eaves | .................. | A61B 6/4405 378/198 |
| 2014/0145085 A1* | 5/2014 | Wu | ....................... | G01T 1/2018 250/366 |

* cited by examiner

IMAGING APPARATUS AND METHODS

CROSS-REFERENCE TO RELATED APPLICATION

The present application is a U.S. continuation patent application of, and claims priority under 35 U.S.C. § 120 to, international patent application serial number PCT/US2013/49504 designating the United States, incorporated by reference herein, which international patent application was filed Jul. 7, 2013, and which international patent application published as WO 2015/005891, incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to imaging apparatus and methods. Preferred embodiments relate to such apparatus and methods used in the context of healthcare, including medical and dentistry as well as other modalities.

Many imaging apparatus and methods are known. Representative such imaging apparatus and methods are disclosed, for example, in U.S. Pat. No. 8,430,563 and U.S. Patent Application Publication No. 2012/0213330, each of which is incorporated herein by reference. Additional patent references disclosing dental and medical imaging apparatus and methods include U.S. Pat. Nos. 5,834,782; 7,016,461; 7,136,452; 7,197,109; 7,319,736; 7,322,746; 7,323,692; 7,336,763; 7,426,258; 7,563,026; 7,596,205; 7,608,834; 7,615,754; and 7,629,587.

Imaging is widely used in healthcare fields, including medical and dental fields. Indeed, with respect to dentistry, according to the EPA approximately 100 million dental x-rays are done each year in the United States. Unfortunately, research studies showed that dental x-rays have been associated with an increased risk of brain and salivary gland tumors, thyroid cancer and low weight birth. Although radiographs are an indispensable diagnostic tool, the increased effective doses of common intraoral and extraoral imaging techniques are high enough to warrant reconsideration of means to reduce patients' exposure. Major concerns arising from the use of ionizing radiation in dentistry are the carcinogenic potential and the adverse effect upon living tissues.

Over the years, dentists have been investigating how to reduce the radiation dose produced by the dental x-ray apparatus and the x-ray beam intensity. These investigations have been focused on the reduction of the kVp, the use of high-speed films, the introduction of dental digital intraoral sensors, collimation and shielding. The deep dose of radiation to critical organs for 90 kVp was generally greater than for 70 kVp. Moreover, it was demonstrated that another practical method to reduce patient exposure time 20-24% is using F speed film in comparison with E speed film. Since its introduction in 1987, exposure times for digital dental imaging are 50 to 80% less than that required for conventional intraoral radiography using E speed film. The typical exposure time required to produce an image for digital dental imaging is approximately 0.05 seconds, this exposure time is far less than the approximately 0.2 seconds required for E speed intraoral film-based radiography. With less radiation exposure, the absorbed dose for the patient is significantly lower. Digital dental imaging decreased 20 to 70% the radiation dose in comparison with F speed film. In addition, rectangular collimation can help reducing radiation dosages by a factor of approximately 3.2 as compared to round collimation. Following the ADA recommendations, a leaded apron with thyroid collar minimizes exposure and should be used when any dental radiograph is taken. Dental radiography either for films or digital sensors requires the use of 65 to 100 kilovolts and from 7 to 15 milliamperes (mA), which can be adjusted according to the individual diagnostic needs of the patients. All-in-all, absorbed doses from dental radiography have declined upwards of 60% in recent years as a result of kVp reduction; faster x-ray film speed, the development of digital sensor technology, x-ray beam collimation and patient shielding.

Despite all of these efforts, the milliamperes (mA) range has not been taken into consideration in any of the attempts of reducing radiation dose to which dental patients are being exposed. The milliamperage is actually the units of the electrical current that is used to produce the radiation. The quantity, or number of x-rays emitted from the tube head, is controlled by the mA. With all other technical factors (e.g., kVp, time) held constant, patient radiation dose is directly proportional to the mA. A 50% in mA reduction results in a decrease in radiation dose by 50%. Radiation reduction in dentistry has been proposed through the introduction of a low dose fluoroscopy technology by considerably minimizing the mA settings and the use of image intensification.

Fluoroscopy is a dynamic x-ray, or x-ray movie, showing images at video frame rates. Due to the limited light produced from the low mA beam at the fluorescent screens, early radiologists were required to sit in a darkened room in which the procedure was to be performed, getting their eyes accustomed to the dark and thereby increasing their sensitivity to the light. The invention of X-ray image intensifiers in the 1950s allowed the image on the screen to be visible under normal lighting conditions, as well as provided the option of recording the images with a conventional camera. Subsequent improvements included the coupling of, at first, video cameras and, later, video CCD cameras permitted recording of moving images and electronic storage of still images.

Recent breakthroughs in imaging made possible the production of low mA settings for dental use as disclosed in U.S. Pat. No. 6,543,936, incorporated herein by reference, by using small image intensifiers in between a detector's converter/plate and collector. Despite these efforts, detector's configuration using the image intensifier and collector is still too bulky to be used inside the mouth and not ergonomic for the dentist to be placed extraorally while performing treatments on patients.

Another disadvantage of intensifiers is image distortion originating from the projection of the x-ray image onto the curved input phosphor, and a smaller component corresponding to the mapping from the input phosphor to the output phosphor and the digital image matrix.

In order to overcome these obstacles, a current attempt of on-chip image intensification for low mA image capturing is known from U.S. Pat. No. 8,430,563 by amplifying the electrical signals within the detector's collecting area reducing a need for image intensifier coupling. However, as of today, none of these dental and medical technologies offer an x-ray imaging method and detector capable of increasing a detector's fill factor to light or quantum efficiency (QE) prior entering a detector's collection area.

QE is a key aspect in determining the photonic outcome of commercial camera sensors. The more light a photodiode can collect, the higher is its QE, and therefore the better the camera performance in low light environments. One of the ways of boosting quantum efficiency in commercial cameras is to add microlenses on top of the sensor chip to collect light and to focus that light onto the collector. Microlens arrays are currently used in order to increase the light collection efficiency of CCD and CMOS sensors for both still photography and videography, as disclosed in U.S. Pat. No. 7,196,388, which is incorporated herein by reference.

The present invention is believed to be an improvement to known imaging apparatus and methods.

SUMMARY OF THE INVENTION

The present invention includes many aspects and features. Moreover, while many aspects and features relate to, and are described in, the context of dentistry, the present invention is not limited to use only in such context, as will become apparent from the following summaries and detailed descriptions of aspects, features, and one or more embodiments of the present invention.

Accordingly, one or more aspects of the present invention relate to use of a microlens in radiography in providing healthcare services, including medical and dental fields. In one or more such aspects, the microlens is included as a component of a detector.

In an aspect of the invention, an imaging method includes the steps of: (a) causing a beam to travel from an emitter through an examination area to a detector; (b) transforming the beam that is received into light; (c) filtering the light; (d) focusing the light onto photosensitive areas of a detector in order to increase the sensitivity to light of the detector where it is transformed into electrical signals; (e) amplifying and converting the electrical signals into digital data representative of digital images; and (f) processing the data representative of digital images for display of digital images to a user.

In a feature, the method further includes the step of displaying the data representative of digital images for display of digital images to a user.

In another aspect of the invention, an imaging method includes the steps of: (a) causing a beam to travel from an emitter through an examination area to a detector; (b) within the detector, performing the steps of, (i) transforming the beam that is received into light, (ii) filtering the light, (iii) focusing the light onto photosensitive areas of the detector in order to increase the sensitivity to light of the detector where it is transformed into electrical signals, (iv) amplifying and converting the electrical signals into digital data representative of digital images, and (v) transmitting the digital data representative of digital images from the detector; and (c) external to the detector, performing the steps of, (i) receiving the digital data representative of digital images transmitted from the detector, and (ii) processing the data representative of digital images for display of digital images to a user.

In a feature, step (b)(iii) is performed using a microlens array located in the detector.

In a feature, the microlens array is made from one of the group of: calcium fluoride; magnesium fluoride; sodium chloride; potassium chloride; thallium bromoiodide; diamond; AMTIR-1; multispectral ZnS; display glasses; silica; fused silica; quartz; polycarbonate; polyester; PEN; acrylate; epoxy resins; acrylic; gallium arsenide; gallium phosphide; germanium; glass; nickel; nickel titanium; stainless steel; plastics; pyrex; sapphire; SF57; high index glass; silicon; zinc selenide; zinc sulfide; and organic light emitting devices.

In a feature, the microlens array is refractive, diffractive, anamorphic, aspherical, spherical, triangular, square, rectangular, hexagonal, octagonal, positive (convex), negative (concave), or center-hollowed.

In a feature, steps (c)(i) and (c)(ii) that are performed external to the detector are performed on a wireless mobile computing device.

In a feature, steps (c)(i) and (c)(ii) that are performed external to the detector are performed on a tablet computing device.

In a feature, steps (c)(i) and (c)(ii) that are performed external to the detector are performed on a smartphone device.

In a feature, the steps performed at the mobile device of processing the data representative of digital images comprises recording the digital data representative of digital images transmitted from the detector.

In a feature, the steps performed at the mobile device of processing the data representative of digital images comprises processing the digital data representative of digital images transmitted from the detector so as to enhance and freeze the represented digital images.

In a feature, the steps performed at the mobile device of processing the data representative of digital images comprises compiling a series of the represented digital images into a video having a video frame rate ranging from 1 to 1000 frames per second.

In a feature, digital images are displayed at the mobile device to a user as still images and in real time video.

In a feature, the steps are performed within the detector such that data representative of a digital image is transmitted to the at the mobile device at a video frame rate of 1 to 1000 digital images per second.

In a feature, the beam caused to be emitted comprises one of the group of (i) electromagnetic radiation and (ii) magnetic resonance.

In a feature, the method further includes the step of displaying the digital images to a user as still images; as real time video; or both.

In a feature, said step (b)(ii) is performed using an autochrome filter; a green filter; a red filter; a blue filter; a green and red filter; a green and blue filter; a red and blue filter; a green, red and blue mosaic filter; a green, red and blue vertically stacked filter; a CYGM (cyan, yellow, green magenta) filter; a RGBE (red, green, blue, emerald) filter; a RGBY (red, green, blue and yellow) filter; panchromatic cells; color co-site sampling; X-trans filter; dichroic mirrors filter; triple-well filter; AR coating filter; broadband AR coating filter; UV coating filter; or UV-enhanced AR coating filter.

In a feature, the detector is an intraoral or internal detector.

In a feature, the detector is an extraoral or external detector.

In another aspect of the invention, a microlens is used within an imaging detector in radiography in providing healthcare services, including medical and dental fields.

In an aspect of the invention, a detector for use in radiography in providing healthcare services includes a converter, a plate, a filter, a microlens, and a collector including photosensitive areas.

In an aspect of the invention, an apparatus for use in radiography in providing healthcare services, comprising a converter, a plate, a filter, a microlens, and a collector including photosensitive areas, an amplifier, an analog-to-digital converter, and a processing unit for processing digital data representative of a view of an area of a patient for presenting a display of such view to a user.

In a feature, the view is displayed in 2D still images.

In a feature, the view is displayed in 3D still images.

In a feature, the view is displayed in real time video.

In a feature, the view is displayed in real time video at 1 to 1000 frames per second.

In an aspect of the invention, an apparatus performs one or more of the foregoing methods.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals.

DETAILED DESCRIPTION

Figure 1:
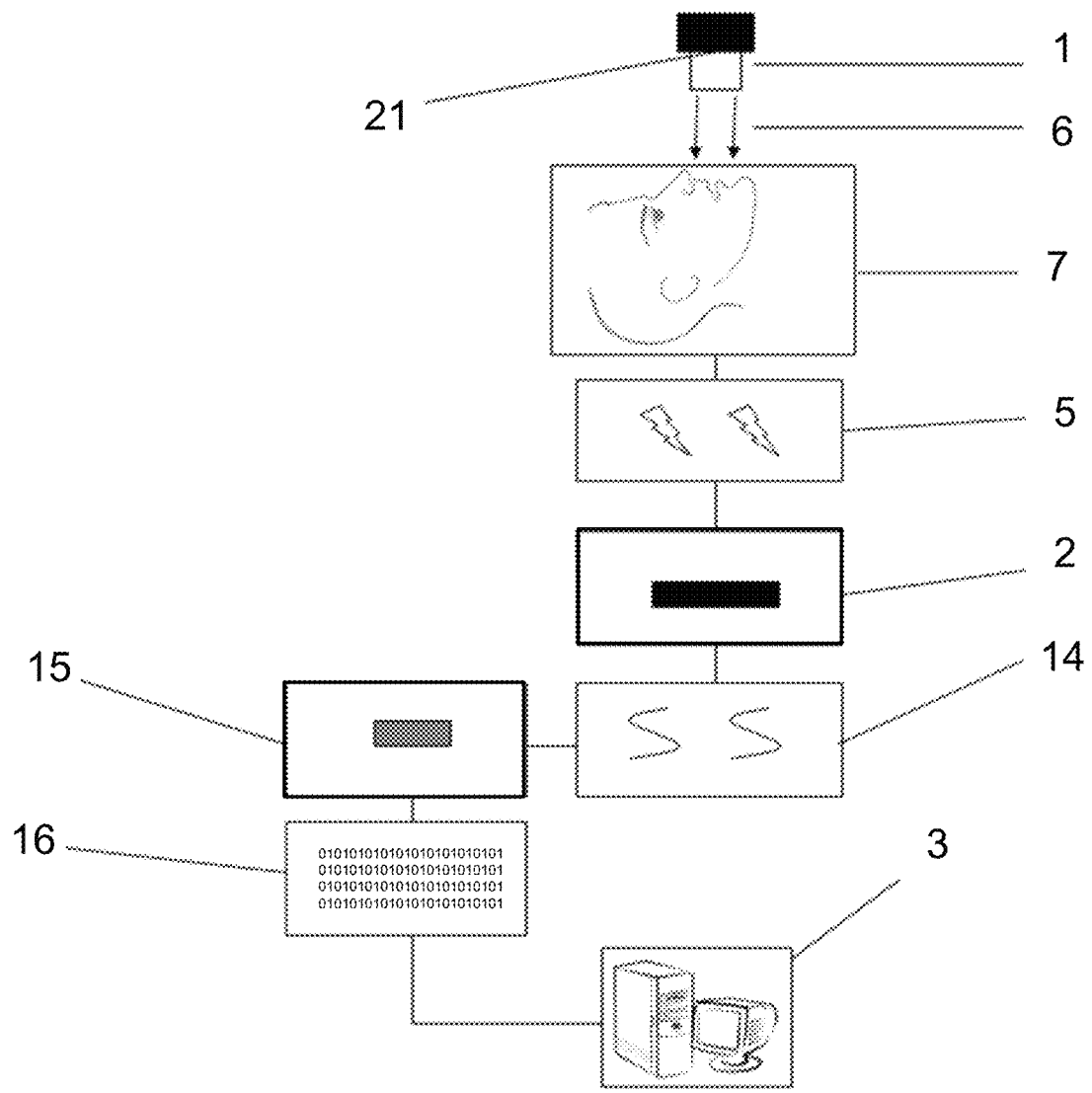
FIG. 1 is a schematic illustration of an imaging apparatus and method in accordance with a preferred embodiment of the invention.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, 16, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

Turning now to FIG. 1, an imaging apparatus and method in accordance with a preferred embodiment of the invention is schematically illustrated. The apparatus comprises an emitter 1, a detector 2, and a computer 3, and is configured and adapted to capture and display low light images 5 as a result of increased quantum efficiency at the detector 2.

In greater detail, the emitter 1 is represented as a rotational emitter with respect to a rotational axis support 21. In other preferred embodiments, the emitter does not rotate. (The rotational feature should be optional for the CBCT scan function, for instance.) The emitter 1 produces a beam 6 that travels through a patient examination area 7 to the detector 2. The beam 6 emitted comprises a region of the electromagnetic spectrum such as gamma rays, x-rays, ultraviolet light, visible light, infrared radiation, terahertz radiation, microwaves, radio frequency (RF), very high frequency (VHF), or ultra-high frequency (UHF) electromagnetic radiation. It is believed that the beam in some embodiments may alternatively comprise magnetic resonance. The beam 6 travels through the patient examination area 7 and reaches the detector 2 as low light images 5 where the low light images 5 are transformed and captured.

Figure 4:
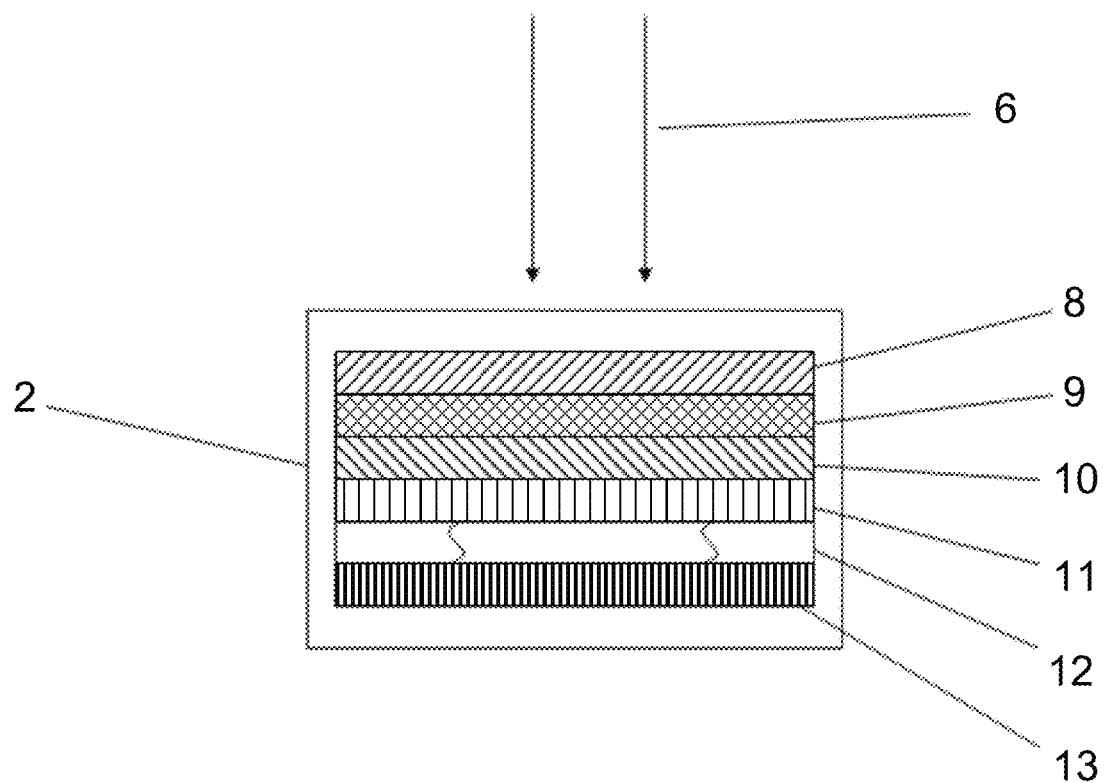
FIG. 4 is a schematic illustration of a detector of used in one or more imaging apparatus and methods in accordance with preferred embodiments of the invention.

The detector 2 is shown in FIG. 1 as an extraoral or external detector. As shown in FIG. 4, the detector 2 comprises a converter 8, a plate 9, a filter 10, a microlens or microlens array 11, and a collector 12 including photosensitive areas 13. The low light images 5 are received at the converter 8 and transmitted directly or through the plate 9 to the filter 10 and then to the microlens array 11. The microlens array 11 is able collect, refine and focus the low light image 5 that would have otherwise fallen onto the nonsensitive areas of the collector 12, thereby enabling low light detection efficiency at the sensitive areas, and thereby increasing the collector 12 fill factor and quantum efficiency.

The filter 10 preferably comprises: an autochrome filter; a green filter; a red filter; a blue filter; a green and red filter; a green and blue filter; a red and blue filter; a green, red and blue mosaic filter; a green, red and blue vertically stacked filter; a CYGM (cyan, yellow, green magenta) filter; a RGBE (red, green, blue, emerald) filter; a RGBY (red, green, blue and yellow) filter; panchromatic cells; color co-site sampling; X-trans filter; dichroic mirrors filter; triple-well filter; AR coating filter; broadband AR coating filter; UV coating filter; or UV-enhanced AR coating filter. The filter 10 may consist of any of the foregoing.

The microlens array 11 preferably is made from one of the following: calcium fluoride; magnesium fluoride; sodium chloride; potassium chloride; thallium bromoiodide; diamond; AMTIR-1; multispectral ZnS; display glasses; silica; fused silica; quartz; polycarbonate; polyester; PEN; acrylate; epoxy resins; acrylic; gallium arsenide; gallium phosphide; germanium; glass; nickel; nickel titanium; stainless steel; plastics; pyrex; sapphire; SF57; high index glass; silicon; zinc selenide; zinc sulfide; or organic light emitting devices.

In addition, the microlens array shape preferably is refractive; diffractive; anamorphic; aspherical; spherical; triangular; square; rectangular; hexagonal; octagonal; positive (convex); negative (concave); or center-hollowed.

The collector 12 preferably is made from one of the groups consisting of: organic, inorganic, or a combination of organic-inorganic materials. Preferably, the microlens array 11 coupling to the collector 12 comprises optical glue or the microlens array 11 coupling to the collector 12 is gapless.

With further reference to FIG. 1, the low light image 5 captured by the photosensitive areas 13 of the collector 12, then is amplified via a high-speed readout amplifier 14, and the resulting electrical signals are then digitally transformed into digital data at the analog-to-digital converter 15. The converter 15 may be on-chip or on a circuit board. The digital data is representative of digital images of the subject located in patient examination area.

As illustrated in FIG. 1, the digital data then is transmitted via transmitter/port 16 to a computer 3. The amplifier 14, converter 15, and transmitter/port 16 as represented in FIGS. 1 and 4 are located outside of the detector 2 itself; however, it is contemplated and, in some embodiments preferred, that these components be located within and form part of the detector 2.

The computer 3 to which the digital data is transmitted via transmitter/port 16 may be a personal computer or a server, and the transmission may be wired or wireless and may be direct or over a network, including a local area network (LAN), wide area network (WAN) or combination thereof, and may be encrypted for security of the data. Various transmission protocols may be used at various logical communication layers, including, for example, WiFi, Bluetooth, Ethernet, and TCP/IP protocols. The digital data is received, processed and displayed to a user as 2D or 3D still images and/or in real time video at 1 to 1000 frames per second. The processing is performed at the computer 3 as illustrated in FIG. 1.

Figure 2:
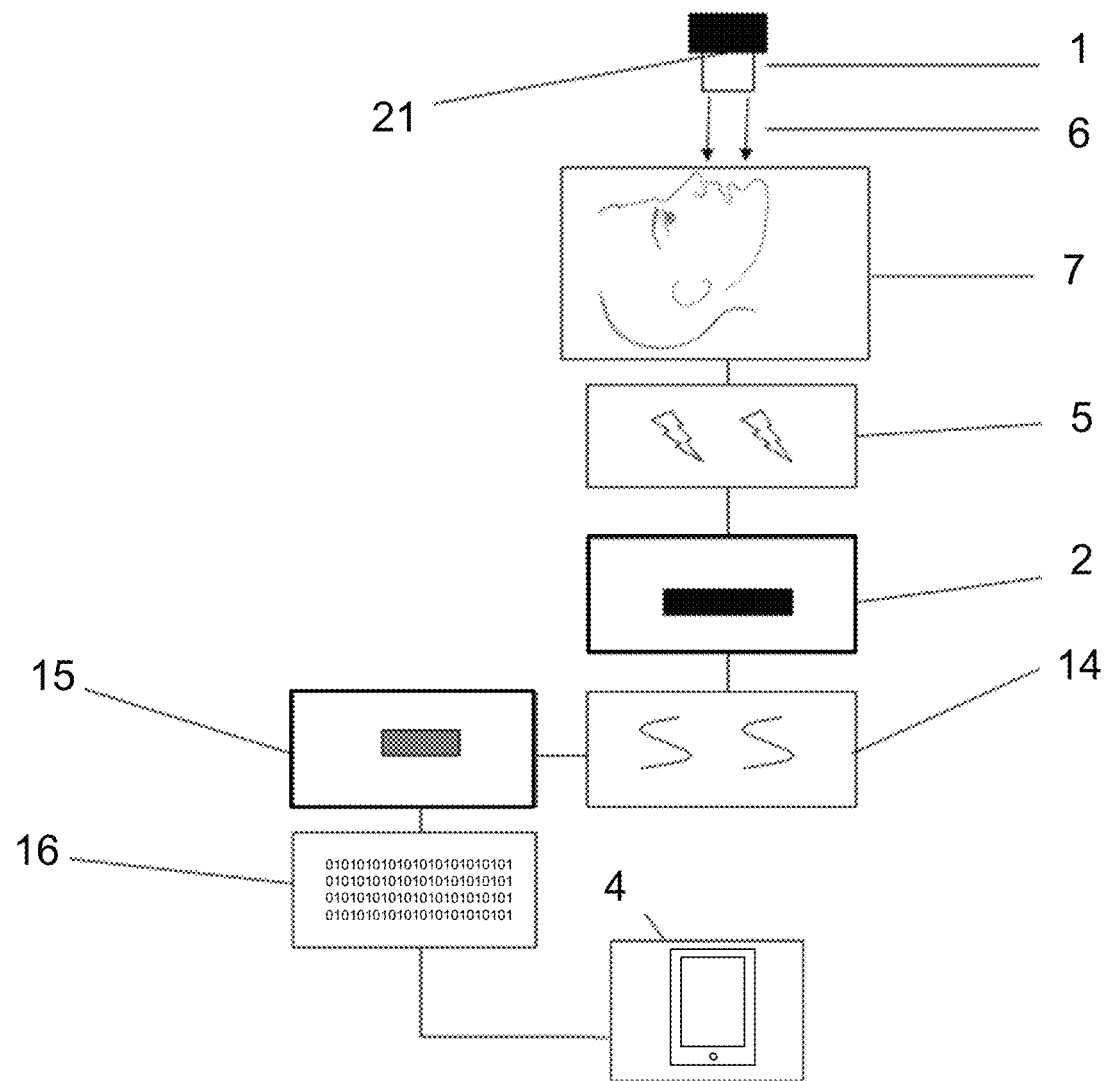
FIG. 2 is a schematic illustration of another imaging apparatus and method in accordance with a preferred embodiment of the invention.

In an alternative embodiment similar to that of FIG. 1, rather than transmitting to a computer 3, the digital data is transmitted to a wireless mobile computing device 4, and the transmission may be wired or wireless and may be direct or over a network, including a LAN, WAN, or combination thereof, and may be encrypted for security of the data. Various transmission protocols may be used at various logical communication layers, including, for example, WiFi, Bluetooth, Ethernet, and TCP/IP protocols. The digital data is received, processed and displayed to a user as 2D or 3D still images and/or in real time video at frame rates of anywhere between 1 and 1000 frames per second, as desired for a particular implementation. The processing is performed at the wireless mobile computing device 4 as illustrated in FIG. 2. The mobile device 4 may comprise a smartphone or tablet computing device, such as iPhones and iPads.

In yet an alternative embodiment similar to that of FIGS. 1 and 2, the digital data is transmitted to a computer 3, and the transmission may be wired or wireless and may be direct or over a network, including a LAN, WAN, or combination thereof, and may be encrypted for security of the data. Various transmission protocols may be used at various logical communication layers, including, for example, WiFi, Bluetooth, Ethernet, and TCP/IP protocols. The digital data is received and processed at the computer 3, and then forwarded on to the mobile device 4 where it is displayed to a user as 2D or 3D still images and/or in real time video at 1 to 1000 frames per second. Communication between the computer 3 and mobile device 4 may be wired or wireless and may be direct or over a network, including a LAN, WAN, or combination thereof, and may be encrypted for security of the data. Various transmission protocols may be used at various logical communication layers, including, for example, WiFi, Bluetooth, Ethernet, and TCP/IP protocols. Alternatively, the processing may be performed at the mobile device 4.

Figure 5:
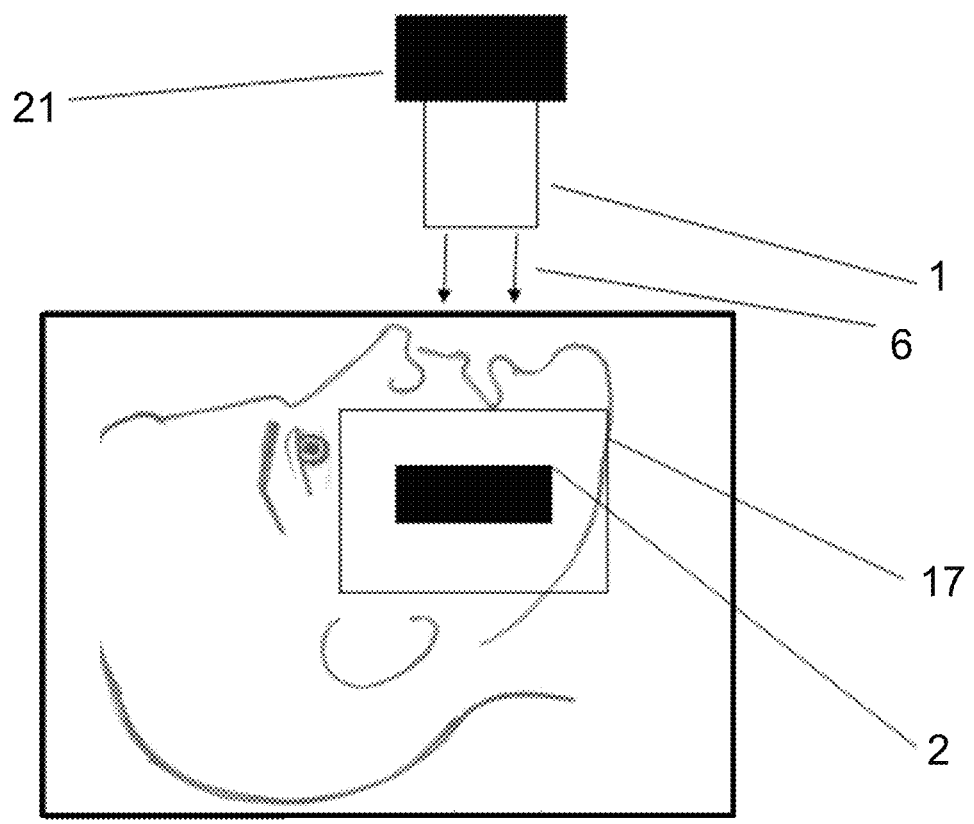
FIG. 5 is a schematic illustration of another imaging apparatus and method in accordance with a preferred embodiment of the invention.

FIG. 5 is a schematic illustration of another imaging apparatus and method in accordance with a preferred embodiment of the invention. As represented in FIG. 5, the detector 2 is in the form of an adult or infant intraoral detector located within an area 17 of a patient's mouth for static and real time video imaging. Furthermore, the emitter 1 is represented as a rotational emitter with respect to a rotational axis support 21; however, the emitter could be fixed, as desired for a particular implementation.

Figure 3:
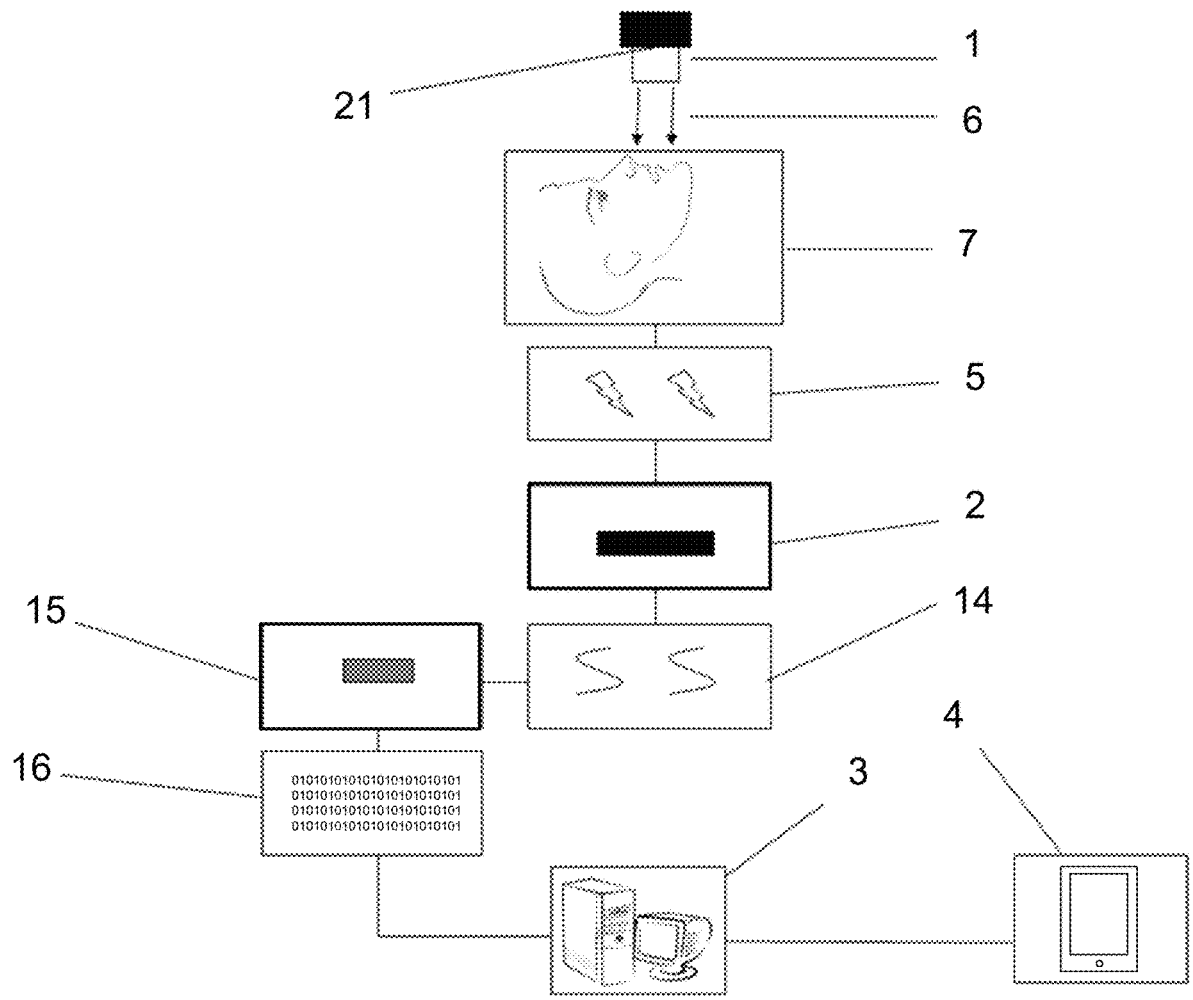
FIG. 3 is a schematic illustration of another imaging apparatus and method in accordance with a preferred embodiment of the invention.

The detector 2 of FIG. 5 alternatively could be in the form of an extraoral or external detector when used outside of the patient's mouth or body for cephalometric, orthopantomographic, scannographic, linear tomographic, tomosynthetic, tomographic, CBCT scan, fluoroscopic, mammography, ultrasound, MRI or frequencies imaging. An extraoral detector 2 is represented in FIGS. 1 through 3. Moreover, a plurality (two or more) of external detectors could be used, together with a corresponding plurality of emitters. The emitters could be parallel, perpendicular, or separated by different degrees. The detectors should mimic the emitters configuration in order that each receives a beam from a respective different emitter. A second external detector could be used, for example, with a second emitter for biplanar or CBCT, MRI or frequencies imaging.

Use of a microlens array in the detector for collecting and focusing light, which would have otherwise fallen on to the non-sensitive areas of the collector, is believed to lead to increased low light collection efficiency, such as the low light image produced at the x-rays detector converter/plate after a low radiation x-ray beam produced by a low mA x-ray source has gone through a patient's examination area. Hence, the use of a microlens array in imaging detectors in-between the converter/plate and the collector is believed to help increase image capture efficiency without compromising sensor's size and image resolution. It is also seen to be advantageous in that there is no necessity to couple or attach additional bulky components, as a microlens array generally is very thin and fits well within a detector.

Consequently, a lower milliamperes (mA) setting at the x-ray source and higher QE at the detector by use of a microlens array is believed to reduce the required radiation dose without impacting image quality. Moreover, it is believed that such imaging apparatus and methods could be applied to all dental and as well as medical imaging technologies, with a dramatic positive impact on public health.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. For example, each of the emitters, detector(s), amplifier(s), and transmitters/ports may be mounted to a wall or ceiling by appropriate supports, or may be handheld and portable. Rotational support apparatus for the emitters and detectors also may be provided as disclosed, for example, in the incorporated references, such as U.S. Pat. No. 8,430,563. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. An imaging method, comprising the steps of:
   (a) causing a beam of electromagnetic radiation in the form of x-rays or gamma rays to travel from an emitter through an examination area to a detector; and
   (b) within the detector, performing the steps of,
      (i) transforming the beam that is received into light,
      (ii) filtering the light,
      (iii) using a microlens array coupled to a collector without a gap between the microlens array and the collector, focusing the light onto photosensitive areas of the collector in order to increase the sensitivity to light of the detector where it is transformed into electrical signals,
      (iv) amplifying and converting the electrical signals into digital data representative of digital images, and
      (v) transmitting the digital data representative of digital images from the detector.

2. The imaging method of claim 1, wherein the microlens array is made from one of the group of: calcium fluoride; magnesium fluoride; sodium chloride; potassium chloride; thallium bromoiodide; diamond; AMTIR-1; multispectral ZnS; display glasses; silica; fused silica; quartz; polycarbonate; polyester; PEN; acrylate; epoxy resins; acrylic; gallium arsenide; gallium phosphide; germanium; glass; nickel; nickel titanium; stainless steel; plastics; pyrex; sapphire; SF57; high index glass; silicon; zinc selenide; zinc sulfide; and organic light emitting devices.

3. The imaging method of claim 1, wherein the microlens array is refractive, diffractive, anamorphic, aspherical, spherical, triangular, square, rectangular, hexagonal, octagonal, positive (convex), negative (concave), or center-hollowed.

4. The imaging method of claim 1, when said step (b)(ii) is performed using an autochrome filter; a green filter; a red filter; a blue filter; a green and red filter; a green and blue filter; a red and blue filter; a green, red and blue mosaic filter; a green, red and blue vertically stacked filter; a CYGM (cyan, yellow, green magenta) filter; a RGBE (red, green, blue, emerald) filter; a RGBY (red, green, blue and yellow) filter; panchromatic cells; color co-site sampling; X-trans filter; dichroic mirrors filter; triple-well filter; AR coating filter; broadband AR coating filter; UV coating filter; or UV-enhanced AR coating filter.

5. The imaging method of claim 1, wherein the detector is an extraoral or external detector when used outside of the patient's mouth or body, or is an intraoral or internal detector for intraoral radiography.

6. The imaging method of claim 1, further comprising,
   (c) performing steps external to the detector of,
      (i) receiving the digital data representative of digital images transmitted from the detector, and
      (ii) processing the data representative of digital images for display of digital images to a user.

7. The imaging method of claim 6, wherein steps (c)(i) and (c)(ii) that are performed external to the detector are performed on a wireless mobile computing device, a tablet computing device, or a smartphone device.

8. The imaging method of claim 6, wherein the step performed of processing the data representative of digital images comprises processing the digital data representative of digital images transmitted from the detector so as to enhance and freeze the represented digital images.

9. The imaging method of claim 6, wherein the step performed of processing the data representative of digital images comprises compiling a series of the represented digital images into a video having a video frame rate ranging from 1 to 1000 frames per second, and wherein the method further comprises the step of displaying digital images to a user as still images and in real time video.

10. The imaging method of claim 6, further comprising a step performed external to the detector of displaying the data representative of digital images for display of digital images to a user.

11. The imaging method of claim 10, further comprising the step of displaying the digital images to a user as 2D or 3D still images and/or as real time video.

12. An imaging method, comprising the steps of:
(a) causing a beam of electromagnetic radiation in the form of x-rays or gamma rays to travel from an emitter through an examination area to a detector; and
(b) within the detector, performing the steps of,
(i) transforming the beam that is received into light,
(ii) filtering the light,
(iii) using a microlens array coupled to a collector using optical glue, focusing the light onto photosensitive areas of the collector in order to increase the sensitivity to light of the detector where it is transformed into electrical signals,
(iv) amplifying and converting the electrical signals into digital data representative of digital images, and
(v) transmitting the digital data representative of digital images from the detector.

13. The imaging method of claim 12, wherein the microlens array is made from one of the group of: calcium fluoride; magnesium fluoride; sodium chloride; potassium chloride; thallium bromoiodide; diamond; AMTIR-1; multispectral ZnS; display glasses; silica; fused silica; quartz; polycarbonate; polyester; PEN; acrylate; epoxy resins; acrylic; gallium arsenide; gallium phosphide; germanium; glass; nickel; nickel titanium; stainless steel; plastics; pyrex; sapphire; SF57; high index glass; silicon; zinc selenide; zinc sulfide; and organic light emitting devices.

14. The imaging method of claim 12, wherein the microlens array is refractive, diffractive, anamorphic, aspherical, spherical, triangular, square, rectangular, hexagonal, octagonal, positive (convex), negative (concave), or center-hollowed.

15. The imaging method of claim 12, further comprising,
(c) performing steps external to the detector of,
(i) receiving the digital data representative of digital images transmitted from the detector, and
(ii) processing the data representative of digital images for display of digital images to a user.

16. The imaging method of claim 15, wherein steps (c)(i) and (c)(ii) that are performed external to the detector are performed on a wireless mobile computing device, a tablet computing device, or a smartphone device.

17. The imaging method of claim 15, wherein the step performed of processing the data representative of digital images comprises processing the digital data representative of digital images transmitted from the detector so as to enhance and freeze the represented digital images.

18. The imaging method of claim 15, wherein the step performed of processing the data representative of digital images comprises compiling a series of the represented digital images into a video having a video frame rate ranging from 1 to 1000 frames per second, and wherein the method further comprises the step of displaying digital images to a user as still images and in real time video.

19. The imaging method of claim 15, further comprising a step performed external to the detector of displaying the data representative of digital images for display of digital images to a user.

20. The imaging method of claim 19, further comprising the step of displaying the digital images to a user as 2D or 3D still images and/or as real time video.

\* \* \* \* \*